United States Patent
Curtis et al.

(10) Patent No.: US 7,471,768 B2
(45) Date of Patent: Dec. 30, 2008

(54) SYSTEMS AND METHODS FOR ESTIMATING PRESENCE OF A MATERIAL WITHIN A VOLUME OF INTEREST USING X-RAY

(75) Inventors: Steven E. Curtis, Salt Lake City, UT (US); R. Larry Anderton, West Jordan, UT (US)

(73) Assignee: General Electric Company, Schenectady, NY (US)

( * ) Notice: Subject to any disclaimer, the term of this patent is extended or adjusted under 35 U.S.C. 154(b) by 66 days.

(21) Appl. No.: 11/369,420

(22) Filed: Mar. 7, 2006

(65) Prior Publication Data

US 2007/0211853 A1 Sep. 13, 2007

(51) Int. Cl.
 *H05G 1/60* (2006.01)
 *H05G 1/64* (2006.01)
(52) U.S. Cl. .............. 378/115; 378/4; 378/98.11; 378/98.12
(58) Field of Classification Search .............. 378/98.11, 378/98.12, 115, 5
 See application file for complete search history.

(56) References Cited

U.S. PATENT DOCUMENTS

| | | | |
|---|---|---|---|
| 5,367,552 A * | 11/1994 | Peschmann | 378/57 |
| 5,600,700 A * | 2/1997 | Krug et al. | 378/57 |
| 5,642,393 A * | 6/1997 | Krug et al. | 378/57 |
| 6,094,467 A | 7/2000 | Gayer et al. | |
| 6,567,496 B1 * | 5/2003 | Sychev | 378/57 |
| 2007/0133736 A1 * | 6/2007 | Chen et al. | 378/5 |

FOREIGN PATENT DOCUMENTS

| | | |
|---|---|---|
| EP | 1037166 A1 | 9/2000 |
| WO | 93/08737 A1 | 5/1993 |
| WO | 03/030738 A1 | 4/2003 |

* cited by examiner

*Primary Examiner*—Edward J. Glick
*Assistant Examiner*—Thomas R Artman
(74) *Attorney, Agent, or Firm*—McAndrews, Held & Malloy; Peter J. Vogel; Michael A. Dellapenna

(57) ABSTRACT

Certain embodiments of the present invention provide a method for x-ray imaging including: exposing a volume of interest to a first technique level to obtain a first set of image data; exposing the volume of interest to a second technique level to obtain a second set of image data; and estimating whether the volume of interest includes a foreign object based at least in part on a comparison of at least an aspect of the first set of image data and at least an aspect of the second set of image data. According to an embodiment, one of the first and second technique levels is selected to generate x-rays having a higher average energy than the other of the first and second technique levels. According to an embodiment, at least one of the first and second technique levels is selectable to cause an overexposure. According to an embodiment, at least one of the first and second technique levels corresponds to a clinical technique level.

25 Claims, 5 Drawing Sheets

FIG. 2

| Element | 1/μ @ 80 keV | 1/μ @ 110 keV | 1/μ Ratio | Ratio of Ratios Calcium to Iron | Ratio of Ratios Calcium to Nickel |
|---|---|---|---|---|---|
| Iron | 0.233 | 0.435 | 0.535 | 1.17 | 1.24 |
| Nickel | 0.161 | 0.318 | 0.507 | | |
| Calcium | 1.77 | 2.83 | 0.628 | | |

200

SYSTEMS AND METHODS FOR ESTIMATING PRESENCE OF A MATERIAL WITHIN A VOLUME OF INTEREST USING X-RAY

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present application relate generally to recognizing a material within a volume of interest using x-ray. Particularly, certain embodiments of the present application relate to recognizing the presence of materials, such as metallic implants or metallic tools that may impact a quality of an x-ray image if such materials are unaccounted for.

Generally speaking, an x-ray imaging system generates image data by exposing a volume of interest to x-rays, and then detecting x-rays with a detector after they have passed through the volume of interest. Some of the x-ray energy is absorbed or attenuated while passing through the volume of interest. X-ray attenuation is the decrease in the number of photons in an x-ray beam due to interactions with the elements (atoms) of a material substance. The amount of x-ray attenuation depends on the elemental composition of the volume of interest. Different elements have different x-ray attenuation properties. As the x-rays travel through a volume of interest, such as a chest cavity, portions of the x-ray beam are attenuated by differing amounts. Thus, if an x-ray beam was substantially uniform before passing through the volume of interest, it becomes non-uniform after passing through the volume of interest. The resulting non-uniform shadow of x-ray energy may be detected by the detector as x-ray image data. For example, bone is generally a better attenuator of x-rays than soft tissue and air. This is because calcium (an element commonly found in bone) is a better attenuator of x-rays than nitrogen, carbon, hydrogen, and oxygen (elements commonly found in soft tissue and air). Thus, bone may appear darker than surrounding soft-tissue in an x-ray image.

At some time during or subsequent to detection, x-ray image data may be converted into a digital format. The digitized x-ray image data may need further processing before a clinician views or diagnoses the images. Image processing, such as gray scale processing, may be used on the digitized x-ray image data to improve the appearance and clinical usefulness of the x-ray image data. Certain types of post-detection processing, such as gray scale mapping and histogram manipulation, are known to be helpful for automatically adjusting x-ray image data. Post-detection processing may generate image data that is more helpful to a clinician than unprocessed x-ray image data.

One method of post-detection processing involves adjusting the brightness and contrast of x-ray image data. For example, a clinician may wish to view an x-ray image of a chest cavity to view the boney vertebral column in the media steinum region of a patient. The clinician may not be as interested in the nearby soft tissue, such as the lungs. Because the vertebrae are relatively good attenuators of x-rays, these bones may appear darker than the surrounding soft-tissue. Resulting images may be too dark for the clinician to resolve finer detail in the bones. Therefore, a post-detection processing algorithm may brighten the entire image. By doing this, the bone will become brighter, and finer detail may become more apparent to the clinician. At the same time, the brighter soft tissue areas may become washed out—i.e. detail becomes lost in the brightened image because brightening causes saturation. This may be an acceptable tradeoff, nonetheless, because in this example, the clinician is primarily interested in the detail of bone, and not surrounding soft tissue. Thus, post-detection processing may involve a tradeoff between optimizing darker areas versus optimizing lighter areas.

For certain radiological applications, post-detection processing may be configured to automatically react to the presence of darker areas. For example, post-detection processing may be configured to automatically brighten x-ray image data if a darker area is detected. This may be advantageous if, for example, the darker area is presumed to be bone, and the clinician is making a diagnosis based on the appearance of the bone. Conversely, post-detection processing may be configured to automatically darken x-ray image data if a lighter area is detected.

The presence of certain foreign objects in a volume of interest, such as an orthopedic implant, may interfere with the intended operation of automatic post-detection processing. In particular, foreign objects that are relatively good attenuators of x-ray energy may interfere with automatic post-detection processing. Automatic post-detection processing may attempt to brighten an entire image to expose detail in a dark area. However, in the case of metal orthopedic implants, for example, a clinician may not wish to see a brightened gray scale for the metal. Moreover, automatic brightening that is sufficient to lighten the very dark metal image may result in excessive brightening of anatomy, thus washing out soft tissue and/or bone. Thus, the automatic post-detection processing may frustrate clinical use of an x-ray image.

Various schemes attempt to correct this gray scale adjustment problem. For example, algorithms that detect the shape of a metal tool or implant may detect the presence of a foreign object in an image. However, such foreign objects may be any of a variety of shapes and sizes. Additionally, patient anatomies and x-ray imaging angles also exhibit a diversity of geometry. Therefore, it may be difficult to provide a cost-effective object detection routine that reliably detects a foreign object within a patient anatomy.

As another example, regionally adaptive image processing routines may adapt or process portions or regions of an image. Regionally adaptive processing routines may, however, still degrade portions of an image where patient anatomy is proximate to a foreign object.

Thus, there is a need for methods and systems that estimate the presence of a foreign object in x-ray image data of a patient. There is a need for methods and systems that compensate automatic post-detection processing in response to an identified presence of a foreign object. Additionally, there is a need for methods and systems that enhance the clinical usefulness of an x-ray image including both anatomy and a foreign object. Moreover, there is a need for methods and systems that adapt subsequent x-ray source generation based on the presence of a foreign object.

BRIEF SUMMARY OF THE INVENTION

Certain embodiments of the present invention provide a method for x-ray imaging including: exposing a volume of interest to a first technique level to obtain a first set of image data; exposing the volume of interest to a second technique level to obtain a second set of image data; and estimating whether the volume of interest includes a foreign object based at least in part on a comparison of at least an aspect of the first set of image data and at least an aspect of the second set of image data. According to an embodiment, the foreign object includes at least one of: a metallic element and an intermetallic element. According to an embodiment, one of the first and second technique levels is selected to generate x-rays having a higher average energy than the other of the first and second technique levels. According to an embodiment, at least one of the first and second technique levels is selectable to cause an overexposure. According to an embodiment, at least one of the first and second technique levels is selectable to cause an underexposure. According to an embodiment, at least one of the first and second technique levels corresponds to a clinical technique level. According to an embodiment, the method further includes adjusting an image processing of at least one of: the first set of image data, the second set of image data, and a subsequent set of image data. According to an embodiment, the method further includes exposing the volume of interest to a subsequent technique level to obtain a subsequent set of image data, wherein the subsequent technique level is adapted based at least in part on the estimation. According to an embodiment, the estimation is based at least in part on a variance between a first data set corresponding to the first set of image data and a second data set corresponding to the second set of image data. According to an embodiment, the method further includes performing, based at least in part on the estimation, at least one of: computed tomography reconstruction, and three-dimensional reconstruction. In an embodiment, the performing includes identifying a estimated foreign object data set and replacing the estimated foreign object data set with a substitute data set. In an embodiment, the substitute data set includes interpolated data from one or more proximately acquired data sets.

Certain embodiments of the present invention provide a system for x-ray imaging including: a first set of image data formable at least in part by exposing a volume of interest to x-rays formed by a first technique level and detecting at least a portion of the x-rays formed by the first technique level with a detector; a second set of image data formable at least in part by exposing the volume of interest to x-rays formed by a second technique level and detecting at least a portion of the x-rays formed by the second technique level with the detector; a foreign object estimation component capable of comparing at least an aspect of the first set of image data and at least an aspect of the second set of image data to form a estimation whether the volume of interest includes a foreign object. According to an embodiment, the foreign object includes at least one of: a metallic element and an intermetallic element. According to an embodiment, one of the first and second technique levels is selected to generate x-rays having a higher average energy than the other of the first and second technique levels. According to an embodiment, at least one of the first and second technique levels is selectable to cause at least one of: an overexposure and an underexposure. According to an embodiment, at least one of the first and second technique levels corresponds to a clinical technique level. According to an embodiment, the system further includes an image processing component capable of adapting an image processing routine based on the estimation. According to an embodiment, the system further includes an x-ray technique processing component capable of adapting a subsequent technique level based on the estimation.

Certain embodiments of the present invention provide a computer-readable storage medium including a set of instructions for a computer, the set of instructions including: a comparison routine for comparing at least an aspect of a first set of x-ray image data with at least an aspect of a second set of x-ray image data, the first set of x-ray image data and the second set of x-ray image data both corresponding substantially to a volume of interest; and a estimation routine for generating a estimation whether a foreign object is present in the volume of interest based at least in part on the comparing at least an aspect of the first set of x-ray image data with at least an aspect of the second set of x-ray image data. According to an embodiment, the estimation is based at least on a perceived variation in attenuation of x-rays between the first set of x-ray image data and the second set of x-ray image data. According to an embodiment, the first set of x-ray image data is generatable at least in part by providing a first technique level to an x-ray source to form x-rays having a first average energy, and the second set of x-ray image data is generatable at least in part by providing a second technique level to the x-ray source to form x-rays having a second average energy, wherein one of the first and second average energies is greater than the other of the first and second average energies. According to an embodiment, the set of instructions further includes an image processing routine capable of processing x-ray image data in response to the estimation to create a clinically helpful x-ray image. According to an embodiment, the set of instructions further includes an x-ray technique processing routine capable of adapting a subsequent x-ray technique level in response to the estimation, to achieve a clinically improved x-ray image. In an embodiment, the set of instructions further includes performing x-ray imaging based at least in part on the estimation. In an embodiment, the x-ray imaging includes at least one of: computed tomography, two-dimensional imaging, and tomosynthesis. In an embodiment, the x-ray imaging is performable by substituting at least a portion of the x-ray image data with substitute data. In an embodiment, the substitute data includes interpolated data.

BRIEF DESCRIPTION OF SEVERAL VIEWS OF THE DRAWINGS

FIG. 2 shows table of monoenergetic x-ray attenuation coefficients for iron, nickel, and calcium.

Figure 1:
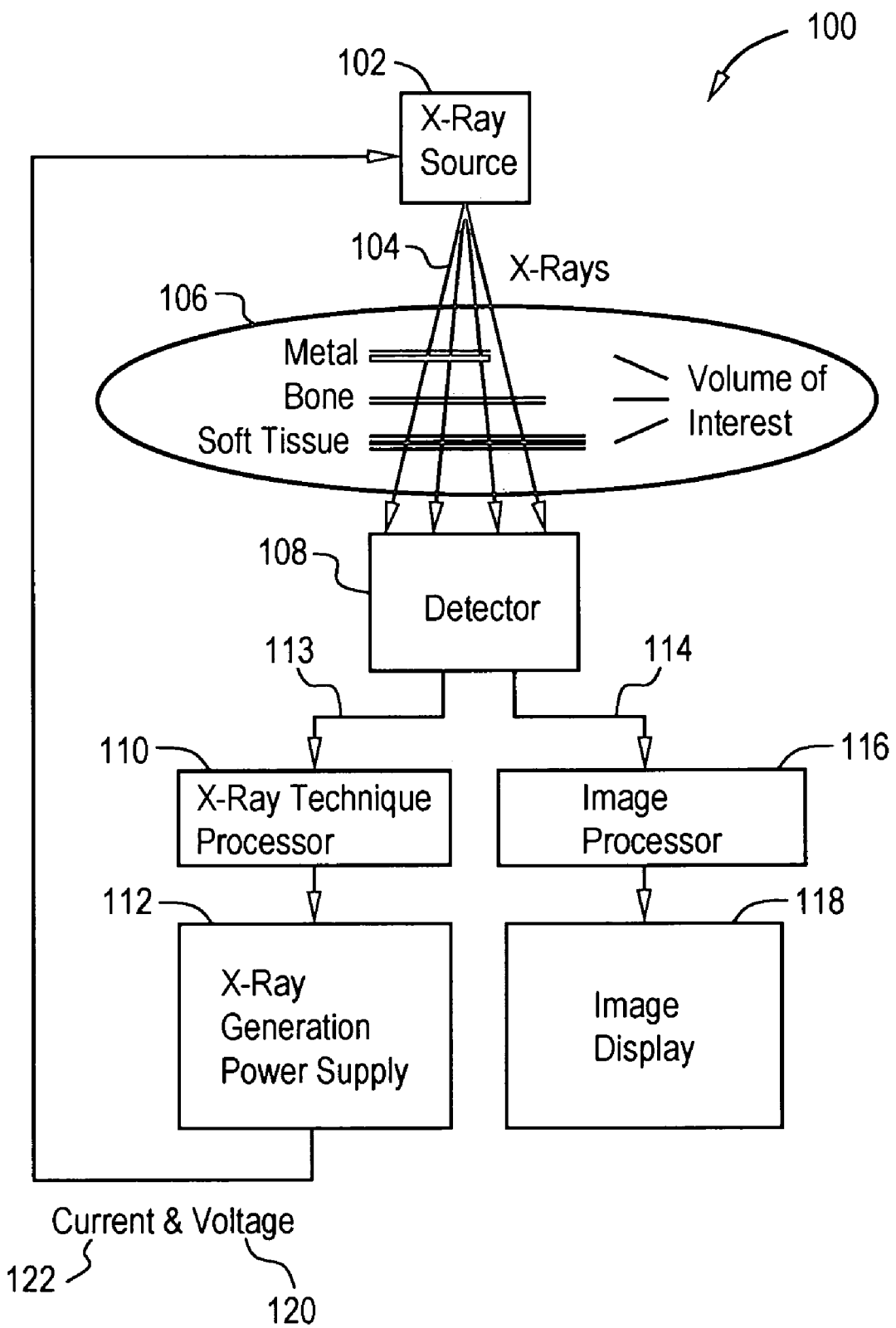
FIG. 1 shows an x-ray imaging system according to an embodiment of the present invention.

The foregoing summary, as well as the following detailed description of certain embodiments of the present application, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 shows an x-ray imaging system 100 according to an embodiment of the present invention. An x-ray source 102 may generate x-rays 104, for example. The x-rays 104 may be generated by the x-ray source 102 during a period of time or interval and/or may be generated continuously (e.g. fluoroscopy), for example. For example, an x-ray source 102 may include a sealed glass bottle containing internal components ("x-ray tube insert"). In side the x-ray tube insert, electrons may be emitted from a metal filament-cathode and accelerated across a voltage potential and through a vacuum to strike a tungsten-based metal anode, for example. As the electrons strike the anode, energy is released in the form of x-ray photons, for example. The cathode-to-anode electron flow in the vacuum is a current 122 and the cathode-to-anode potential is a voltage 120, for example. Both the current 122 and voltage 120 may be controlled by the x-ray generation power supply 112, for example.

An x-ray source 102 may generate x-rays 104 when a voltage 120 and current 122 are provided to the x-ray source 102. The voltage 120 may be a relatively high voltage, measurable in kilovolts, for example. For example, the voltage 120 may range from 30 kV to 150 kV. The current 122 may be a relatively low current, measurable in milliamps, for example. For example, the current 122 may range from 0.020 mA to 1000 mA. A particular combination of voltage 120 and current 122 provided to the x-ray source 102 may be called a technique level, for example. For example, one technique level may have a voltage 120 of 56 kV and a current 122 of 1.1 mA. A second technique level may have a voltage 120 of 81 kV and a current of 1.1 mA, for example.

A technique level having a corresponding voltage 120 and current 122 may be provided to an x-ray source 102 for a period of time, or an interval, for example. For a given technique level, the x-ray source 102 may generate x-rays 104 having a corresponding average energy, for example. While individual x-ray photons 104 may have any of a distribution of energies, the overall average energy level of x-rays 104 has an energy that corresponds to at least one particular technique level, for example. A technique level that has a lower power (power=current 122*voltage 120) may cause the x-ray source 102 to generate x-rays 104 with a lower average energy, for example. Conversely, a technique level that has a higher power may cause the x-ray source 102 to generate x-rays 104 with a higher average energy, for example. For example a technique level of 56 kV and 1.1 mA may cause the x-ray source 102 to generate x-rays 104 with a lower average energy, than, for example a technique level of 81 kV and 1.1 mA. While average x-ray energy may be correlated to a technique level, there need not exist any specific type of proportional relationship (e.g. linear, exponential, quadratic, etc.) between average x-ray energy and technique level, for example.

The x-rays 104 may travel through a volume of interest 106, for example. A volume of interest 106 may include a human patient, or a portion thereof, for example. A volume of interest 106, such as patient anatomy, may include a variety of substances, for example. For example, as shown in FIG. 1, a volume of interest 106 may include a foreign object, bone, and soft tissue. A volume of interest 106 may also include gaseous substances, such as air or vapor, for example. The various substances in a volume of interest may each include a variety of elements, for example. A foreign object, such as an implant for example, may include one or more metallic and/or inter-metallic elements, for example. For example, an orthopedic implant may include iron, titanium, nickel, or other elements (e.g., elements that may comprise stainless steel,) for example. Bone may include calcium, for example. Soft tissue may include hydrogen, carbon, oxygen, and/or other elements, for example.

As the x-rays 104 travel through the volume of interest 106, some of the x-rays 104 may be absorbed or scattered by portions of the volume of interest 106, for example. X-ray 104 attenuation may be related to the type and thickness of element(s) within the attenuating medium. For example, various elements have linear attenuation coefficients that correspond to a given monoenergetic x-ray energy. The linear attenuation coefficient for an element may vary for different x-ray energies, for example. FIG. 2 shows a table 200 of monoenergetic x-ray attenuation coefficients for iron, nickel, and calcium. A reciprocal of a linear attenuation coefficient ($1/\mu$) is given for two different x-ray energies—80 keV and 110 keV, for example. It may be surmised from table 200 that each element attenuates x-rays to a different degree depending on the energy of the x-ray, for example. Furthermore, the column labeled "$1/\mu$ Ratio" shows that the degree of this variance may depend on the type of element, for example. The last two columns show that the elements may be distinguished based on the difference of each element's degree of variance in attenuation response, for example. In other words, the last two columns show that it may be possible to differentiate calcium from iron, and calcium from nickel based on each elements varying attenuation of x-rays in response to different x-ray energies, for example.

The elements shown in table 200 are only for illustrative purposes, and it may be possible to differentiate any element based on the variance of attenuations across x-ray energies, for example. For example, it may be possible to differentiate carbon, oxygen, hydrogen, titanium, nitrogen, or any other element, because each element has a characteristic attenuation curve across different x-ray energies. While table 200 shows elemental attenuation responses to monoenergetic x-rays (only one x-ray energy), it should be understood that the principle expressed by table 200 may also be useful to understanding elemental attenuation responses to polyenergetic x-rays having an average energy, for example. In other words, although x-ray energy may not be monoenergetic, the principles expressed by table 200 may be exploited to differentiate between elements in a volume of interest, for example.

Using the principles outlined in table 200, it may be possible to estimate whether particular element(s) are within the volume of interest by exposing the volume to at least two different x-ray energies, for example. Assume, for example, that a volume of interest contains boney areas of a patient's hip, and that it is unknown whether the patient has a metal alloy implant containing iron and/or nickel in his hip, and hence whether these attenuated areas should be brightened (if bone) or not brightened (if metal), for example. Looking at table 200, it may be seen from the $1/\mu$ Ratio that iron and nickel have a greater attenuation variance in response to 80 keV and 110 keV x-rays than does calcium. Note, that a $1/\mu$ ratio of 1 indicates that an element would exhibit no attenuation variance between 80 keV and 110 keV, for example. Calcium has a $1/\mu$ ratio closer to unity than does iron and nickel, and therefore has a lesser attenuation variance in response to 80 keV and 110 keV, for example. Assume that the volume is exposed first to 80 keV x-rays and then to 110 keV x-rays, for example. Assume also that calcium is the most significant attenuator of x-rays in hip anatomy, if no implant exists, for example. If iron and/or nickel are substantially present in the hip anatomy, then the drop off in attenuation will be greater at 110 keV than a hip without iron and/or nickel substantially present, for example. Therefore, the percentage increase in non-attenuated x-rays will be greater at 110 keV for a hip anatomy having a substantial amount of iron and/or nickel, than for a hip without iron and/or nickel, for example. Exploiting these principle(s), it may be possible to estimate the presence of substantial amounts of certain elements within a volume of interest, for example.

Turning back to FIG. 1, at least a portion of x-rays 104 pass through the volume of interest 106, and at least a portion of them may be detected by a detector 108, for example. The detector 108 may convert the x-rays 104 into an electronic signal that may be further processed, for example. For example, the detector 108 may include of a solid-state panel using selenium or silicon-based technology, or the detector may use an image intensifier tube and associated camera, or a microchannel plate with fiber optic reducer and associated camera, for example. Outputs from the detector may include x-ray image signal data that may be processed as explained below.

The signal 114 may be provided to an image processor 116, and a related signal 113 may be provided to an x-ray technique processor 110, for example. The image processor 116 may receive the signal 114, and process the signal 114, for example. The image processor 116 may process the signal 114 to enhance the image data, for example. The image processor 116 may process a signal 114 containing one or more sets of image data, for example. For example, a signal 114 may contain two or more sets of image data, corresponding to two or more x-ray exposure intervals. The image data of the signal 114 may be enhanced for clinical purposes, for example. For example, certain tissues in a volume of interest 106 may be clinically relevant. A radiologist may wish, for example, to analyze detail of a patient's bone, and thus bone tissue may be clinically relevant, for example. An image processor 116 may provide an output signal corresponding to one or more processed sets of image data, for example. For example, an image processor 116 may receive two or more sets of image data in signal 114, and may provide one enhanced set of image data as an output.

An image processor 116 may incorporate a variety of known image processing methods, for example. For example an image processor 116 may employ spatial noise filters, temporal noise filters, grayscale filters, grayscale adjustment routines, contrast adjustment routines, brightness adjustment routines, color adjustment routines, spatial edge enhancement routines, color filters, and the like. For example, image processor 116 may be capable of detecting the darkest shade of gray in a set of image data. It may be necessary to first filter image data for excessive noise spikes before detecting the darkest shade of gray in a set of image data, for example. After the darkest shade of gray is detected in a set of image data, an image processor may adjust gray scale, brightness and/or contrast of a set of image data in response to the darkest detected shade of gray, for example.

After processing signal 114, image processor 116 may provide processed image data to an image display 118, for example. An image display 118 may display an image that corresponds to the volume of interest 106, for example. An image display 118 may be a cathode ray tube, a liquid crystal display, or the like, for example. A clinician, such as a radiologist, may view the image on the image display 118 for clinical purposes and/or otherwise, for example.

An x-ray technique processor 110 may receive a technique processor signal 113 related to or even identical to image processor signal 114, for example. Technique processor signal may come from detector 108 and/or image processor 116, for example. An x-ray technique processor 110 may be part of an image processor 116, or may be a separate device altogether, for example. An x-ray technique processor 110 may process signal 113 similar to how image processor 116 processes a signal, for example. For example, x-ray technique processor 110 may detect a darkest, brightest, and/or average shade of gray in a set of image data from signal 113, for example. In response to the processing of signal 113, x-ray technique processor 110 may determine a technique level 120, 122 to be provided to x-ray source 102 for subsequent imaging, for example. In other words, x-ray technique processor 110 may form part of a feedback loop to x-ray source 102, whereby a technique level 120, 122 applied to x-ray source 102 may be adjusted in response to a detected signal 113, for example. For example, the power of a technique level 120, 122 may be increased if not much x-rays 104 reach the detector 108. The x-ray technique processor 110 may provide a signal, information, and/or instructions to an x-ray generation power supply 112, for example. The x-ray generation power supply may be capable of receiving the signal, information, or instructions and generating in response a current 122 and voltage 120 for subsequent x-ray imaging iterations, for example.

Figure 3:
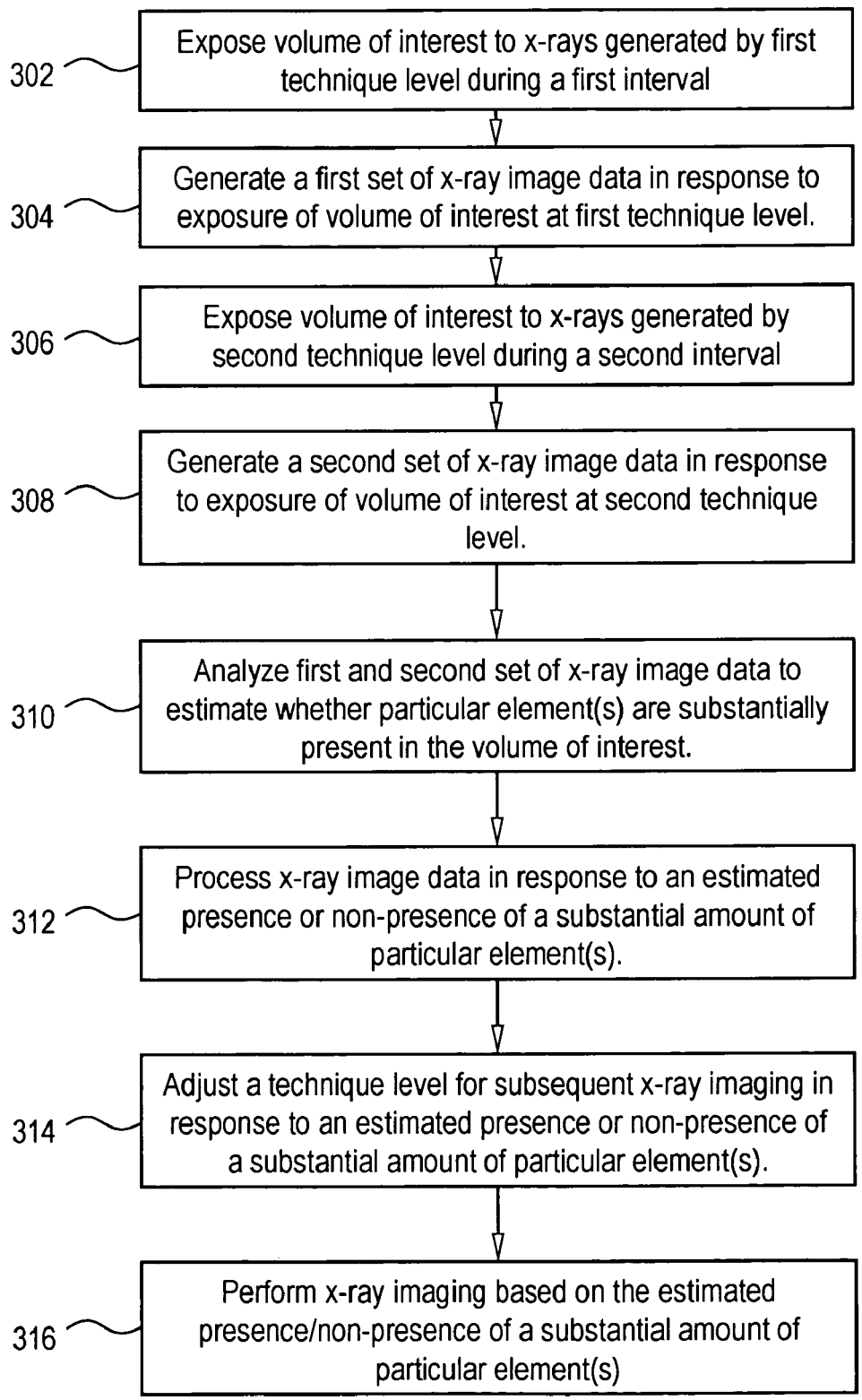
FIG. 3 shows a flow diagram for a method for x-ray imaging in accordance with an embodiment of the present invention.

FIG. 3 shows a flow diagram for a method 300 for x-ray imaging in accordance with an embodiment of the present invention. The steps of method 300 may be performed in an alternate order as shown, for example. At least some of the steps of method 300 may be performed simultaneously or substantially simultaneously, for example. Furthermore, some steps of method 300 (or portions thereof) may be omitted (e.g. steps 312 and/or 314), for example. The steps of method 300 may be performed by a computer and/or processor (such as image processor 116 and/or x-ray technique processor 110 shown in FIG. 1) executing a set of instructions on a computer-readable medium, for example.

Method 300 may be employed for detecting a foreign object within a volume of interest, for example. As discussed, a foreign object may include specific types of metallic and inter-metallic elements, for example. For example, a foreign object such as an orthopedic implant may include iron and/or nickel. Method 300 may be employed for identifying any of a variety of element(s) of interest, either individually or in combinations, such as iron and/or nickel, for example. If element(s) of interest are detected, image processing methods may be adapted or adjusted accordingly, for example. Additionally, if element(s) of interest are detected, subsequent x-ray generation technique levels may be adapted or adjusted accordingly, for example.

At step 302, a volume of interest may be exposed to x-rays generated by an x-ray source at a first technique level during one or more intervals. For example, the x-ray source and x-rays may be similar to x-ray source 102, and x-rays 104 (both shown in FIG. 1). Step 302 may involve exposing the volume of interest to a series of x-ray bursts over a series of intervals at a first technique level, for example. The x-rays generated in response to the first technique level may be polyenergetic, and may have a distribution of energies, for example. The x-rays, though polyenergetic, may have an average energy that corresponds to the first technique level, for example. Certain elements of the volume of interest may attenuate x-rays more effectively than other of the elements in the volume of interest, for example. For example, metallic objects such as an orthopedic implant may attenuate x-rays more effectively than soft tissue.

At step 304, a first set of x-ray image data is generated in response to the exposure of the volume of interest at the first technique level. As discussed in step 302, there may be more than one exposure at the first technique level, for example. A first set of x-ray image data may be generated by detecting x-rays at a detector, such as detector 108 (shown in FIG. 1), for example. A detector may then generate a corresponding signal, such as signal 114 (shown in FIG. 1) containing the first set of x-ray image data, for example.

At step 306, the volume of interest may be exposed to x-rays generated by an x-ray source at a second technique level during one or more intervals. For example, the x-ray source and x-rays may be similar to x-ray source 102, and x-rays 104 (both shown in FIG. 1). Step 306 may involve exposing the volume of interest to a series of x-ray bursts over a series of intervals at a second technique level, for example. The x-rays generated in response to the second technique level may be polyenergetic, and may have a distribution of energies, for example. The x-rays, though polyenergeteic, may have an average energy that corresponds to the second technique level, for example. The second technique level may cause the x-ray source to produce x-rays with an average energy that differs from the average x-ray energy corresponding to the first technique level, for example. The average x-ray energy at step 306 may differ from that of step 302 so as to exploit elemental response characteristics, such as those shown in table 200, for example. The elemental attenuations in response to the first technique level (e.g. from step 302) and the second technique level may be such that a substantial presence of particular element(s) becomes estimatable, for example.

Either of the first or second technique level may be selected for clinical x-ray imaging of a patient's anatomy, for example. It should be understood that a technique level for clinical x-ray imaging may vary based on a patient's weight, the anatomy to be imaged, and/or various other factors, for example. For example, more x-ray energy may be required to image larger patients, and larger volumes of interest. Additionally, either the first or second technique level may be intended to cause a higher exposure, and possibly an overexposure, for example. The exposure of x-rays in response to the technique level may be such that clinical detail in the resulting x-ray image may appear washed out, or otherwise unclear, for example. Similarly, the first or second technique level may be intended to cause a lower exposure, and possibly an underexposure, for example. Overexposure or underexposure technique levels may be helpful in exploiting the attenuation response variation of certain elements (see table 200, for example), for example. According to an embodiment, at least one of the first and second technique levels corresponds to a clinical technique level (e.g. a technique level that may result in clinically usable image data).

At step 308, a second set of x-ray image data is generated in response to the exposure of the volume of interest at the second technique level. As discussed in step 306, there may be more than one exposure at the second technique level, for example. A second set of x-ray image data may be generated by detecting x-rays at a detector, such as detector 108 (shown in FIG. 1), for example. A detector may then generate a corresponding signal, such as signal 114 (shown in FIG. 1) containing the second set of x-ray image data, for example.

At step 310, the first and second sets of x-ray image data may be analyzed to estimate whether particular element(s) are substantially present in the volume of interest. For example, an image processor (such as image processor 116 in FIG. 1), and/or an x-ray technique processor (such as x-ray technique processor 110 in FIG. 1) may be capable of detecting a substantial presence of a particular element within the volume of interest. It may be possible to compare aspects of the first and second sets of x-ray image data to detect for a substantial presence of an element of interest, for example. For example, it may be possible to compare a dark shade of gray (e.g. the darkest shade or another appropriate shade for comparison) in the first and second sets of x-ray image data to estimate whether a substantial presence of an element of interest exists. It may also be possible to compare the average brightness of the first and second sets of x-ray image data to make an estimation, for example. Comparison of the first and second sets of x-ray image data may be done manually such as through user interaction, or automatically such as by image processing software routines, or by a combination thereof, for example.

At step 312 x-ray image data may be processed in response to whether element(s) of interest were estimated. Image data processing may include computed tomography reconstruction and/or three-dimensional reconstruction discussed below in conjunction with FIGS. 4 and 5, for example. For example, if an element of interest is detected, then auto-processing methods may be adjusted or adapted. X-ray image data used for processing may come from either of the first or second sets of x-ray image data, generated in steps 304, 308, especially if either of these sets of image data were generated with a clinically helpful technique level (e.g. not overexposed or underexposed), for example. Additionally, x-ray image data for processing may come from previously or subsequently generated sets of x-ray image data, for example. For example, as will be discussed below in conjunction with step 314, the estimation of a foreign object may be used to adapt subsequent technique levels for x-ray source generation. The adapted technique level may be more appropriate for generating clinically helpful x-ray images for a volume of interest with a foreign object, for example. Thus, a subsequent set of x-ray image data generated with an adapted technique level may be used for image processing at step 312, for example.

Image data may be processed by image processor auto-adjustment routines that assist the clinician with clinical objectives, for example. However, the substantial presence of certain elements (for example nickel and/or iron in a metal alloy tool or metal alloy implant) may interfere with the auto-adjustment routines if unaccounted for, for example. Therefore, image processor auto-adjustment routines may be adjusted or adapted to account for substantial presence of these interfering element(s) of interest, for example. For example, with no substantial metal estimated in the volume of interest, auto-adjustment routines may brighten all or regional parts of the image such that the darkest areas, like bone, are adjusted to be more clinically useful, for example. At the same time lighter areas near the bone, like soft tissue, may also be brightened to a point that there is slightly less clinical usefulness but still acceptable, for example. However, if the dark(est) areas are metal (rather than bone, for example), and auto-adjustment routines do not account for the presence of metal, the brightening adjustment from these routines may be stronger because a metal image may originally be even darker than bone, for example. With stronger brightening to the regions containing metal and anatomical tissue in close proximity to metal, anatomical tissue may be brightened to a degree that renders the image less clinically useful than if there had been no metal present, for example. However, by accounting for the presence of metal in a region of the volume of interest, the auto-adjustment routines may lower the degree of brightening in such a region, for example. Consequently, the tissue within that region may not be brightened to the point of being less clinically useful, for example.

At step 314, a technique level for subsequent x-ray imaging may be adjusted in response to a estimated presence or non-presence of a substantial amount of a particular element(s). The x-ray technique processor auto-adjustment routines may serve to brighten the image viewed on the image display, for example. While the image processor auto-adjustment routines may adjust brightness to certain regions of the image, auto-adjustment routines may adjust brightness of the entire image viewed on the image display by increasing (or decreasing) the average energy of the x-rays through the volume of interest, for example. For example, with no substantial metal estimated in the volume of interest, auto-adjustment routines may adjust the overall brightness of the image such that the darkest areas, like bone, may be adjusted to be more clinically useful, for example.

Similarly, lighter areas in the image, like soft tissue, may also be brightened to a point that there is slightly less clinical usefulness but still acceptable usefulness, for example. But if the darkest areas are metal (rather than bone, for example), and auto-adjustment routines do not account for the presence of metal, the brightening effect from increased x-ray energy caused by the auto-adjustment routines may be even stronger because metal may be darker than bone, for example. With stronger brightening to the general image from a volume of interest containing metal and anatomical tissue, this tissue may be brightened to a degree that renders the image less clinically useful than if there had been no metal present, for example. However, by accounting for the presence of metal in the volume of interest, auto-adjustment routines may lower the amount of average x-ray energy through the volume of interest, and the anatomical tissue within the volume of interest may not be brightened to the point of being less clinically useful, for example.

At step 316, x-ray imaging may be performed based at least in part on the estimated presence/non-presence of a substantial amount of particular element(s). For example, subsequent x-ray imaging may be performed with adjusted technique levels and/or image processing as discussed above. X-ray imaging parameters including x-ray intensity, gating, timing, angulation, and/or the like may be adjusted based on the estimated presence/non-presence of a substantial amount of particular element(s), for example. For example, if certain computed tomography x-ray angles appear to go through metal, then those angles may be subsequently omitted during step 316. Such omission may reduce image artifacts resulting from metal, for example. X-ray imaging may include two-dimensional "shadowgrams", computed tomography, tomosynthesis, and/or the like, for example.

The following is an illustrative example of how method 300 may be performed in accordance with an embodiment of the present invention. A patient's hip is to be imaged that has a stainless steel orthopedic implant containing iron and nickel. The system auto-adjustment routines is set up to brighten the darkest areas of the image, assuming (as routine defaults) that the volume of interest does not contain metal. At step 302, the hip is exposed to x-rays resulting from a first technique level. The first technique level has been selected for clinical purposes—to resolve detail in the boney structure of the hip. At step 304, a first set of x-ray image data is generated by an x-ray detector in response to the exposure in step 302. At step 306, the hip is exposed to x-rays resulting from a second technique level. The second technique level was selected to cause an overexposure. While the overexposure may not be helpful for resolving clinical detail, it may be useful in highlighting the variance in attenuation responses for iron, nickel, and calcium. At step 308, a second set of x-ray image data is generated by an x-ray detector in response to the exposure in step 306.

At step 310, the first and second sets of x-ray image data (resulting from images acquired at different average x-ray energies) are compared to estimate whether an iron and/or nickel implant is in the patient's hip. An image processor (similar to image processor 116) performs the calculation and estimation routines to make this estimation. The methodology used for this estimation may be similar/identical to methods that take advantage of differing linear attenuation coefficients associated with various elements, as illustrated in table 200, and as described elsewhere.

After it is estimated that there is a substantial presence of iron and/or nickel in the patient's hip (e.g. a foreign object), x-ray image data processing is adapted to account for the presence of the metallic orthopedic implant at step 312. If no substantial amount of iron and/or nickel is present, the x-ray image data is processed by an image processor (similar to image processor 116 shown in FIG. 1) to automatically adjust the brightness and contrast of x-ray image data for clinical purposes. However, if a relatively dark orthopedic implant is present, it will interfere with the automatic image adjustment process, which may result in substandard x-ray images for clinical purposes. Therefore, the estimation from step 310 is communicated to the automatic image adjustment process. The automatic image adjustment process now accounts for the substantial presence of iron and/or nickel, and automatically adjusts the brightness and contrast of the x-ray image data in light of the estimation. The x-ray technique processor adjustments may interact with the overall detector dynamic range capability in such a way as to increase or lessen the detector's ability to preserve gray scale differentiation in either very bright areas of the image (for higher energy technique levels) or very dark areas of the image (for lower energy technique levels). For example, if technique level is increased, gray scale differentiation is lessened in bright areas and gray scale differentiation in dark areas may be increased, and visa versa. Thus, the optimization of the auto-adjustment routines may serve to preserve/enhance needed dynamic range capacity in bright or dark areas of the image. This may be accomplished by increasing to a greater degree the technique level if the darker regions of the image are resulting from denser anatomy (such as bone), and by increasing to a lesser degree (if at all) the technique level if the darker regions of the image are resulting from metal. This may enhance the effectiveness of auto-adjustment routines described elsewhere, wherein these auto-adjustment routines enhance the image if metal is present/not present in the volume of interest, and wherein the auto-adjustment routines require sufficient gray scale differentiation to be available prior to enhanced processing.

In addition to adapting the automatic adjustment process, the estimation also is used to automatically adjust a subsequent technique level for generating x-rays, in step 314. In this particular example, an x-ray technique processor (similar to processor 110 in FIG. 1) receives the estimation from the image processor. The x-ray technique processor then determines a technique level for subsequent x-ray imaging. This is accomplished by the establishing a gray scale brightness desired set point value that represents the desired overall brightness of the image. This overall desired value may be a combined weighted mix of average, maximum, and minimum brightness within all or some portion of the image, and weighted in some combination. The actual combined value resulting from the volume of interest is measured and compared against the desired set point. If the initial x-ray technique level is too low in energy the x-ray technique processor increases the technique level until the actual and desired values match. If there is metal in the volume of interest the desired set point is lowered to avoid driving the actual combined value to be too high for obtaining an optimal image. Or, if there is metal in the volume of interest the weighting of the mix of average, maximum, and minimum is altered to avoid driving the technique level too high. For example, the weight of the minimum brightness may be lowered. Other combinations and/or methods of auto-adjusting the x-ray technique level may be used to achieve enhanced imaging results, for example.

Figure 4:
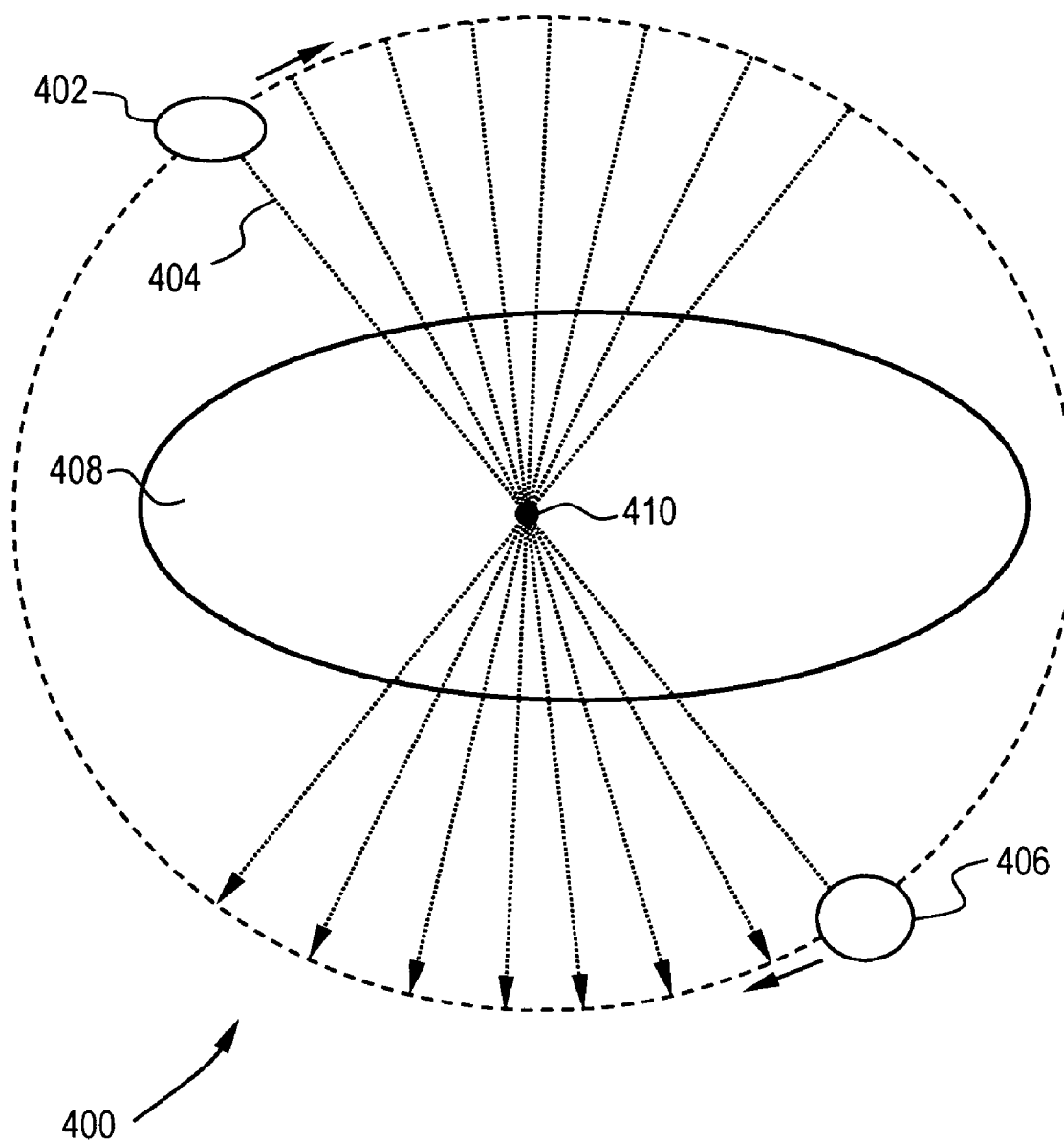
FIG. 4 shows an illustration of computed tomography imaging, in accordance with an embodiment of the present invention.

FIG. 4 shows an illustration of computed tomography imaging 400, in accordance with an embodiment of the present invention. It may be helpful to detect the presence of metal in x-ray data acquired when performing Computed Tomography (CT) or 3 Dimension Reconstruction (3D Reconstruction) imaging, for example. CT imaging 400 may be performable by moving an x-ray source 402 (which may be in many respects similar to source 102, shown in FIG. 1) in conjunction with a substantially opposite image receptor 406, for example. A volume of interest 408 may be located between the source 402 and receptor 406, for example. The x-ray source 402 and image receptor 406 may substantially rotate about the volume of interest 408 in such a way as to obtain data sets corresponding to the volume of interest 408 over a plurality of angles, for example. These angles may be spaced about 1 degree apart and may cover a total arc of 200 degrees, for example. Other spacing and total arc values may also be used, depending on x-ray dose(s), the time required to obtain data set(s), the desired accuracy of the resultant reconstruction, and the reconstruction algorithm(s), for example. The data sets corresponding to the plurality of angles may be combined together to reconstruct attenuation characteristics within the volume of interest 408, for example. This may be called back projection, for example.

Conceptually, back projection may be understood in the following manner. Back projection may strive to provide improved focus (e.g. resolution, sharpness, clarity, and/or the like) for a desired region 410, or voxels ("volumetric pixels"), while providing reduced focus (e.g., increased blurring) for other regions (or other voxels) located within the volume of interest 408 but in a different location from the specific voxel (s) 410 to be reconstructed, for example. To perform back projection, data sets may be collected on a plurality or substantially all voxels within the volume of interest 408, for example. An image receptor 406 having a plurality of pixels may facilitate the collection of data sets containing a plurality or substantially all voxels within the volume of interest 408, for example. With an image receptor 406 having a plurality of pixels, data sets may be collected simultaneously for a plurality voxels, for example. If the voxels of interest are located in a relatively thin slice of anatomy, a single CT reconstruction ("slice") may be performed, for example. If the voxels of interest are located over a region thicker than a single "slice", then a 3D reconstruction may be performed, for example. One way to envision a 3D reconstruction may be to reconstruct multiple CT slices stacked in tandem, for example. Various algorithms may exist to accomplish both CT and 3D reconstructions, and some of the algorithms may incorporate other methods than those described herewith, for example.

Figure 5:
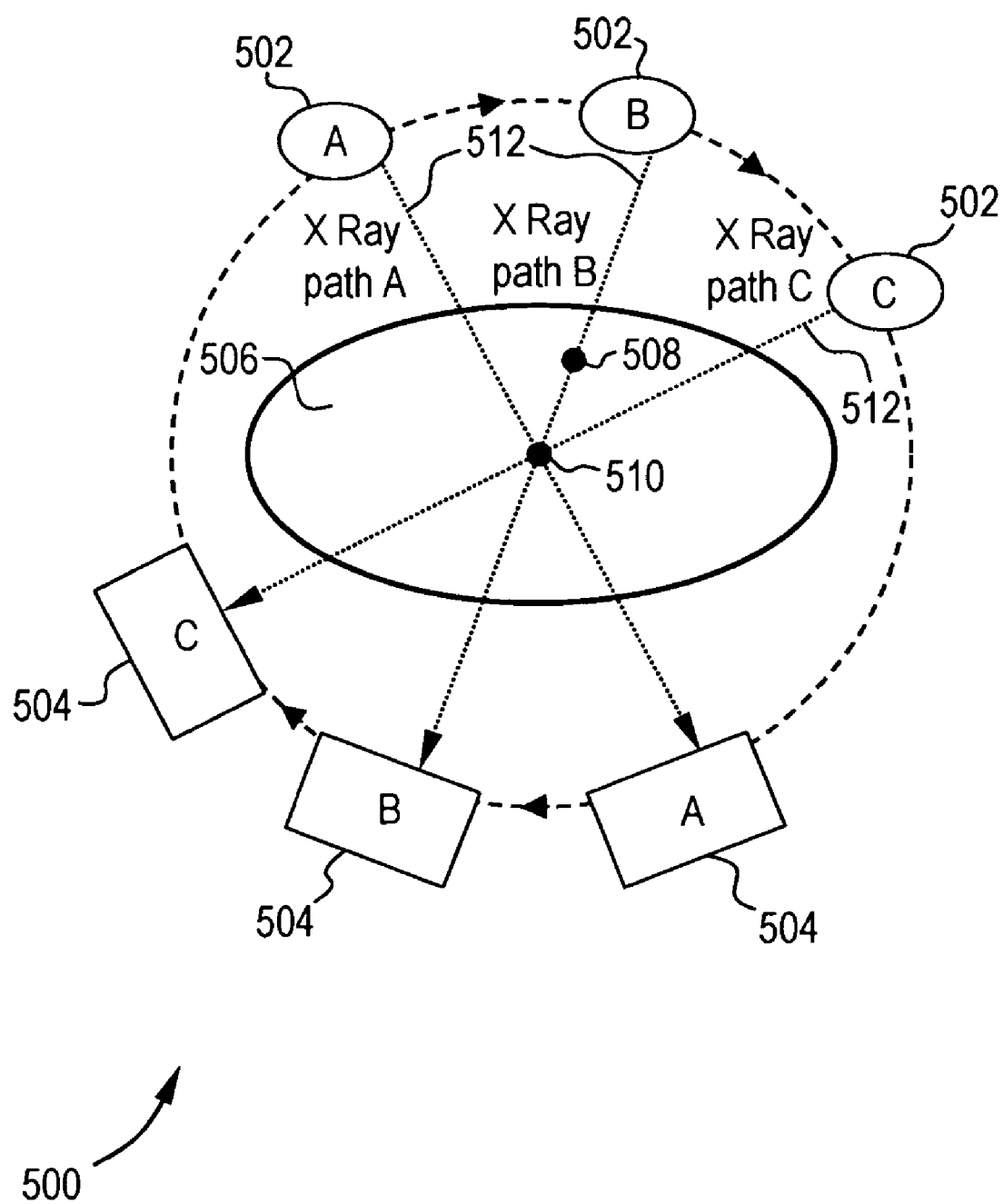
FIG. 5 illustrates an example of computed tomography of a volume of interest including a substantial presence of metal, in accordance with an embodiment of the present invention.

FIG. 5 illustrates an example of computed tomography 500 of a volume of interest 506 including a substantial presence of metal, in accordance with an embodiment of the present invention. CT and 3D Reconstruction algorithms may create artifacts that distort associated attenuation reconstruction for one or more voxels, for example. A cause of artifacts may be the presence of metal within a volume of interest 506, for example. Because a substantial presence of metal 508 may create a relatively strong attenuation effect, x-ray paths 512 that pass at least partially through voxel(s) containing metal 508 may cause distortion when reconstructing other voxels that are anatomical and non-metal along the same x-ray path, for example. The blurring effect mentioned earlier may not be as effective when the attenuation away from the voxel(s) of focus 510 is too strong, as may occur from other voxel(s) containing metal 508, for example. There may be several methods used to reconstruct voxel(s) in back projection. One technique may be to employ the Fourier Slice Theorem, which may result in attenuation values for each voxel under reconstruction, for example. The Fourier Slice Theorem, and other voxel reconstruction algorithms or techniques may perform with higher fidelity when data sets are acquired along a plurality angles, as explained previously, for example. However, it may be possible to use certain voxel reconstruction algorithms even if data from some angles are missing, degraded, flagged as erroneous, and/or the like, for example. If the volume of interest 506 contains metal in certain regions, it may be preferable to account for the data taken at angles where x-rays pass through the voxel(s) being reconstructed 510 and that also pass through voxel(s) containing metal 508, for example. Data obtained from a path comprising voxel(s) containing metal 508 may be replaced, for example, with extrapolated data derived from x-ray paths 512 which do not pass through metal but which also are close neighbors to paths of x-rays 512 that did pass through metal, for example. For example, x-ray paths A and C may represent x-ray paths 512 that do not pass through metal 508 but do pass through an anatomical voxel to be reconstructed 510. Further, x-ray path B may represent x-ray path(s) 512 that pass at least partially through voxel(s) containing metal 508 and the voxel to be reconstructed 510. Thus, one method of improving CT and 3D Reconstruction of an anatomical voxel to be reconstructed 510 may be to account for data acquired that also passed through metal 508, for example. If x-ray paths A and C are sufficiently close to x-ray path B, then data acquired at the image receptor in position B and for the pixel associated with x-ray path B may be identified and replaced (or altered, e.g.) with interpolated value(s) from data at image receptor pixels associated with x-ray paths A and C in image receptor positions A and C respectively, for example. There may be other methods to manage and use (or not use) data that is known to have passed through metal between the x-ray source and the image detector, for example.

As discussed above, x-ray image data may be obtained at lower and higher energy technique level levels to estimate the presence/non-presence of metal. The technique level methods, e.g., using lower and higher x-ray technique levels may be adapted to CT and 3D Reconstruction processes, for example. In CT and 3D Reconstruction processes, the x-ray source 502 may provide x-rays at higher and lower technique levels for each angle during data set acquisition, for example. The resulting data sets may be examined (e.g., via software and/or hardware) to determine if any of the x-ray paths indicate a substantial presence metal along an x-ray path 512, for example. The attenuation of the x-rays along any path 512 may be examined at the higher and lower poly-energetic technique levels, for example. By comparing the attenuations between the two technique levels, the presence/non-presence of metal along the path 512 may be estimated for one or more specific angle(s) of orientation of the x-ray source 502 and image receptor 504, for example. Once a presence/non-presence of metal has been estimated, the estimation may be accounted for and used appropriately in the back projection or reconstruction of voxels via methods discussed above, or via other methods not discussed but used for voxel back projection or reconstruction, for example. For example, method 300 may be suitably adapted to perform CT and/or 3D Reconstruction for volumetric data as discussed.

In an embodiment, an x-ray imaging system, such as system 100 shown in FIG. 1, includes a computer-readable medium, such as a hard disk, floppy disk, CD, CD-ROM, DVD, compact storage, flash memory and/or other memory. The medium may be in an image processor, x-ray technique processor, and/or image display (similar components shown in FIG. 1) and/or in a separate system. The medium may include a set of instructions capable of execution by a computer or other processor. The comparison and estimation functions described above may be implemented as instructions on the computer-readable medium. For example, the set of instructions may include a comparison routine that compares an aspect of first and second sets of x-ray image data, such as darkest shade of gray, average brightness, strength of received signal, and/or other aspects. Additionally, the set of instructions may include a estimation routine that estimates the presence of a foreign object in a volume of interest based on information generated in the comparison routine and the principles of x-ray attenuation (e.g. table 200). In an embodiment, a estimation may be formed by a estimation based on a perceived variation in attenuation between a first and second set of x-ray data, for example.

Thus, embodiments of the present application provide methods and systems that estimate the presence of a foreign object in x-ray image data of a patient. Additionally, embodiments of the present application provide methods and systems that compensate automatic post-detection processing in response to an identified presence of a foreign object. Embodiments of the present application provide methods and systems that enhance the clinical usefulness of an x-ray image including both anatomy and a foreign object. Moreover, embodiments of the present application provide methods and systems that adapt subsequent x-ray source generation based on the presence of a foreign object.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. For example, features may be implemented with software, hardware, or a mix thereof. Therefore, it is intended that the invention not be limited to the particular embodiment disclosed, but that the invention will include all embodiments falling within the scope of the appended claims.

The invention claimed is:

1. A method for x-ray imaging comprising:
    exposing a volume of interest to a first technique level to obtain a first set of image data, wherein said volume of interest comprises human tissue;
    exposing said volume of interest to a second technique level to obtain a second set of image data; and
    estimating whether said volume of interest comprises a foreign object based at least in part on a comparison of at least an aspect of said first set of image data and at least an aspect of said second set of image data, wherein at least one of said first and second technique levels is selected to cause at least one of: an overexposure and an underexposure.

2. The method of claim 1, wherein said foreign object comprises at least one of: a metallic element and an intermetallic element.

3. The method of claim 1, wherein one of said first and second technique levels is selected to generate x-rays having a higher average energy than the other of said first and second technique levels.

4. The method of claim 1, wherein at least one of said first and second technique levels corresponds to a clinical technique level.

5. The method of claim 1 further comprising adjusting an image processing of at least one of: said first set of image data, said second set of image data, and a subsequent set of image data.

6. The method of claim 1 further comprising exposing said volume of interest to a subsequent technique level to obtain a subsequent set of image data, wherein said subsequent technique level is adapted based at least in part on said estimation.

7. The method of claim 1, wherein said estimation is based at least in part on a variance between a first data set corresponding to said first set of image data and a second data set corresponding to said second set of image data.

8. The method of claim 1 further comprising performing, based at least in part on said estimation, at least one of: computed tomography reconstruction, and three-dimensional reconstruction.

9. The method of claim 8, wherein said performing comprises identifying a estimated foreign object data set and replacing said estimated foreign object data set with a substitute data set.

10. The method of claim 9, wherein said substitute data set comprises interpolated data from one or more proximately acquired data sets.

11. A system for x-ray imaging comprising:
    a first set of image data formable at least in part by exposing a volume of interest to x-rays formed by a first technique level and detecting at least a portion of said x-rays formed by said first technique level with a detector, wherein said volume of interest comprises human tissue;
    a second set of image data formable at least in part by exposing said volume of interest to x-rays formed by a second technique level and detecting at least a portion of said x-rays formed by said second technique level with said detector;
    a foreign object estimation component capable of comparing at least an aspect of said first set of image data and at least an aspect of said second set of image data to form a estimation whether said volume of interest comprises a foreign object, wherein at least one of said first and second technique levels is selected to cause at least one of: an overexposure and an underexposure.

12. The system of claim 11, wherein said foreign object comprises at least one of: a metallic element and an intermetallic element.

13. The system of claim 11, wherein one of said first and second technique levels is selected to generate x-rays having a higher average energy than the other of said first and second technique levels.

14. The system of claim 11, wherein the x-ray imaging is for at least one of: computed tomography reconstruction, and three-dimensional reconstruction.

15. The system of claim 11, wherein at least one of said first and second technique levels corresponds to a clinical technique level.

16. The system of claim 11 further comprising an image processing component capable of adapting an image processing routine based on said estimation.

17. The system of claim 11, further comprising an x-ray technique processing component capable of adapting a subsequent technique level based on said estimation.

18. A computer-readable storage medium including a set of instructions for a computer, the set of instructions comprising:
    a comparison routine for comparing at least an aspect of a first set of x-ray image data with at least an aspect of a second set of x-ray image data, said first set of x-ray image data and said second set of x-ray image data both corresponding substantially to a volume of interest, wherein said volume of interest comprises human tissue; and an estimation routine for generating a estimation whether a foreign object is present in said volume of interest based at least in part on said comparing at least an aspect of said first set of x-ray image data with at least an aspect of said second set of x-ray image data, wherein said first set of x-ray image data is generatable at least in part by providing a first technique level to an x-ray source to form x-rays having a first average energy, and said second set of x-ray image data is generatable at least in part by providing a second technique level to said x-ray source to form x-rays having a second average energy, wherein one of said first and second average energies is greater than the other of said first and second average energies, and wherein at least one of said first and second technique levels is selected to cause at least one of: an overexposure and an underexposure.

19. The set of instructions of claim 18, wherein said estimation is based at least on a variation in attenuation of x-rays between said first set of x-ray image data and said second set of x-ray image data.

20. The set of instructions of claim 18 further comprising an image processing routine capable of processing x-ray image data in response to said estimation to create a clinically helpful x-ray image.

21. The set of instructions of claim 18 further comprising an x-ray technique processing routine capable of adapting a subsequent x-ray technique level in response to said estimation.

22. The set of instructions of claim 18 further comprising performing x-ray imaging based at least in part on said estimation.

23. The set of instructions of claim 22, wherein said x-ray imaging comprises at least one of: computed tomography, and three-dimensional reconstruction.

24. The set of instructions of claim 23, wherein said x-ray imaging is performable by substituting at least a portion of said x-ray image data with substitute data.

25. The set of instructions of claim 24, wherein said substitute data comprises interpolated data.

* * * * *